(12) United States Patent
Kuehnle et al.

(10) Patent No.: US 6,706,394 B2
(45) Date of Patent: Mar. 16, 2004

(54) METHOD AND APPARATUS FOR MANUFACTURE OF MAGNETIZABLE MICROPARTICLES

(76) Inventors: Manfred R. Kuehnle, 22 Deer Run Rd., Lincoln, MA (US) 01773-2507; Adelheid Kuehnle, 3119 Beaumont Woods Pl., Honolulu, HI (US) 96822

( * ) Notice: Subject to any disclaimer, the term of this patent is extended or adjusted under 35 U.S.C. 154(b) by 95 days.

(21) Appl. No.: 09/847,965

(22) Filed: May 2, 2001

(65) Prior Publication Data

US 2002/0098359 A1 Jul. 25, 2002

Related U.S. Application Data

(60) Provisional application No. 60/201,088, filed on May 2, 2000.

(51) Int. Cl.$^7$ .................................................. G11B 5/66
(52) U.S. Cl. .................. 428/402; 428/403; 428/404; 428/407; 428/329; 428/694 BA; 428/900; 427/127; 427/216; 427/221; 435/173.1; 436/526
(58) Field of Search ................................ 428/329, 401, 428/403, 404, 634 BA, 900, 407; 435/173.1; 427/127, 46, 221; 436/526

(56) References Cited

U.S. PATENT DOCUMENTS

| | | |
|---|---|---|
| 4,345,588 A | 8/1982 | Widder et al. |
| 4,454,234 A * | 6/1984 | Czerlinski .................... 436/526 |
| 4,554,088 A | 11/1985 | Whitehead et al. |
| 5,427,675 A | 6/1995 | Toyama et al. |
| 5,516,670 A * | 5/1996 | Kuehnle et al. .......... 435/172.3 |
| 5,698,271 A | 12/1997 | Liberti et al. |

OTHER PUBLICATIONS

Tibbe AGJ, de Grooth BG, Greve J., Liberti PA, Dolan GJ, Terstappen, L., WMM (1999) "Optical tracking and detection of immunomagnetically selected and aligned cells", *Nature Biotechnology* 17:1210–1213.

Allen, L.M., Kent, T., Wolfe, C., Ficco, C., Johnson, J. (1997) "A Magnetically Targetable Drig Carrier for Paclitaxel" *Scientific and Clinical Applicationsof Magnetic Carriers, Häfeli et al.*, Plenum Press, New York, pp. 481–493.

Matthews, R.E.F. (1997) "Preliminarysolationof the Virus" *Plant Virology*, 3rd ed. AcademicPress, Inc., San Diego, pp. 59–60.

Maulik, S., Patel, S.D. (1997) "Re-engineeringthe Immune Response" *MolecularBiotechnology*, Wiley–Liss, New York, pp. 154–185.

(List continued on next page.)

*Primary Examiner*—Leszek Kiliman
(74) *Attorney, Agent, or Firm*—Saliwanchik, Lloyd & Saliwanchik

(57) ABSTRACT

The subject invention related to methods and apparatuses for the manufacture of magnetizable carrier particles. In addition the subject invention pertains to particles having one or more of a variety of particle configurations and/or functional features. These geometric particle configurations and/or functional features such as delivering or removing a pay load can be tailored to achieve one or more desired missions. The subject invention also pertains to a method and apparatus for the delivery of particles to target materials, in order to accomplish one or more of a variety of missions. In a specific embodiment of the subject invention, acicular and other particles with a lengthwise dimension that are substantially uniform and homogenous in their geometry are manufactured and provided with magnetizations. In this way, predictable mechanical force responsivity can be achieved when these particles are subjected to an external magnetic field gradient.

39 Claims, 10 Drawing Sheets

(2 of 10 Drawing Sheet(s) Filed in Color)

OTHER PUBLICATIONS

O'Barr R. et al.: "Preparation and Quantitative Magnetic Studies of Single–Domain Nickel Cylinders" *Journal of Applied Physics*, American Institute of Physics. New York, US vol. 79, No. 8, part 2A, Apr. 15, 1996, pp. 5303–5305, XP000695755 ISSN: 0021–8979 p. 5304, column 1–column 2, paragraph 2; Figures 2, 3.

Tayaoka A. et al.: "Preparation of CO–FE–P Amorphous Fine Needles with Anodization Technique and Measurement of Demagnetizing Factor" *Journal of Applied Physics*, American Institute of Physics, New York, US vol. 79, No. 8, Part 2B, Apr. 15, 1996, pp. 6016–6018, Xpooo695001 ISSN: 0021–8979 p. 6016, column 1–column 2, paragraph 2.

* cited by examiner

METHOD AND APPARATUS FOR MANUFACTURE OF MAGNETIZABLE MICROPARTICLES

CROSS-REFERENCE TO A RELATED APPLICATION

This application claims the benefit of U.S. Provisional Application Serial No. 60/201,088, filed May 2, 2000.

BACKGROUND OF THE INVENTION

When conducting genetic manipulations or other treatments of cells or tissue, it is often necessary to partially or completely penetrate the cell walls and/or membranes with a biological or other agent. This penetration is necessary in order to achieve a desired effect on the cell wall and/or internal cellular elements such as the cytoplasm, nucleus, plastids, chromosomes, plasmids, etc. The objective of such a procedure may be, for example, the destruction of selected substances or the production of new or improved biological characteristics. These procedures can be used to modify a plant, animal, or microbe to improve, for example, growth rate, disease resistance, or protein production. Other applications include the tagging of cells for tracking and identification, or the micromanipulation of cells by in situ rotation or displacement in space.

In genetic research, for example, such methods are used to penetrate tissue and cells with particles precoated with DNA encoding genes of interest; cell penetration is followed by DNA delivery into the cell nucleus or organelle. To reach the intracellular space and then the cell subcellular structure, the particles must traverse formidable cell walls and membranes. Because these cell walls are difficult to penetrate, the particles carrying the DNA are driven into the cells by the force of an explosive or an electrical discharge so that the kinetically driven particles smash into the target tissue. Even then, in order to have the necessary kinetic energy for penetration of certain targets and to certain depths, the particles must be several micrometers in diameter. Thus, the implantation process results in appreciable cell damage due to the impact of the particles and/or due to sonic concussion from the particle-propelling discharge. Some cell tissue, drawing upon its natural strength, may recover from this trauma sufficiently to integrate the newly delivered genetic material into its chromosomes; however, a significant percentage of the tissue is unable to do so.

These prior methods of delivering particles to cells also lack sufficient control over particle size distribution, particle coating quality, and the velocity and direction of travel of the particles, resulting in a lack of predictability and reproducibility of the particle delivery technique. The prior delivery techniques are further disadvantaged because they require that the target tissue be maintained in a vacuum which removes moisture from the treated tissue contributing to tissue degradation. Moreover, the apparatus for performing the implantations requires time-consuming set up prior to each implantation cycle and is cumbersome to clean after same so that the throughputs of the apparatus are relatively low.

Other methods employed or suggested for direct gene delivery to cells include the use of microlasers, microbead vortexing, electrofusion, chemical fusion, microinjection, and electroporation. Such techniques all rely on increasing the permeability of the tissue cells by physically, chemically, or electrically disrupting cell walls and/or membranes temporarily; exogenously added DNA may then enter the cell through the temporary ruptures. Some of these methods, including microinjection and fusion of preselected protoplasts or subprotoplasts, require working at the single cell level. This necessitates micromanipulation of the cells, often involving immobilization by agarose plating or pipette suction. Such micromanipulations must be carried out with a microscope placed in the sterile environment of a laminar flow hood, which can be very cumbersome. Also, controlled fusion, for example in the production of somatic hybrids, requires bringing the fusion partners into close proximity which is technically difficult to accomplish. Another bottleneck in plant and other genetic transformation systems is the relative inefficiency of selection following gene transfer. A means to enrich for penetrated cells or organelles prior to, or in place of, selection by use of antibiotics, herbicides, osmotics or toxins would greatly improve the efficiency of a transgenesis system.

A number of magneto-mechanical systems have recently been devised whose purpose is to deliver certain reactive substances to a target site using sharp-tipped microparticles as carriers which penetrate the target sites such as pollen, cells, organisms, etc. to deliver these substances in singular or multiple sequential entries by desorption from the microparticles to cause a change in the target site, such as altering a genetic trait or curing a disease.

U.S. Pat. No. 5,516,670 discloses a method for delivering particles into cellular specimens by means of a non-uniform, convergent magnetic field and is incorporated herein by reference.

There still exists a need for particles which are designed to effectively perform each of a variety of tasks. For example, particles can serve as "payload carriers" such as to either deliver or extract one or more substances of interest to or from target sites. In another example, particles can "mark" the target for detection and/or counting purposes. Particles themselves may be the therapeutic agent, as in heat therapy. In addition, the subject particles can be furnished with properties which enable, or enhance, chemical interactions to achieve the desired treatment goals. Because of the variety of treatments required such as genetic alteration of a cell via DNA coupling or gene splicing or addressing different target sites such as pollen, cells, meristems, or human cancers, tumors, lymph nodes or nerve endings, a wide variety of microparticles are needed in terms of length, width, tips, geometries, and basic materials.

BRIEF SUMMARY OF THE INVENTION

The subject invention provides methods and apparatuses for the manufacture of magnetizable carrier particles ("micromagnets"). In addition, the subject invention pertains to particles having one or more of a variety of particle configurations and/or functional features. These particle configurations and/or functional features can be tailored to achieve one or more desired missions. The subject invention also pertains to methods and apparatuses for the delivery of particles to target materials, in order to accomplish one or more of a variety of missions.

In a specific embodiment of the subject invention, acicular and other particles with a lengthwise dimension that are uniform and homogenous in their geometry are manufactured and provided with magnetizations. In this way, predictable mechanical force responsivity can be achieved when these particles are subjected to an external magnetic field gradient. Preferably, saturation magnetization can be provided to the particles in order to yield optimal force for a particular particle size when inserted into a magnetic field gradient.

In another embodiment of the subject invention, the size, length, cross-sectional area, and/or shape and geometric contours of the particles, including asymmetry of mass, are selected such that the particle is optimally related to the target body. Accordingly, the particle's configuration can vary based on the target's size, shape, resistance against penetration, and other characteristics of the particle. For example, the subject particles can be provided with sharp "tips" at one or both ends. These sharp tips enable the particles to exert powerful pressures (force per unit area) at the point of contact between particle tip and target body, enhancing the ability of the particles to breach a protective wall of the target and to enter its interior space. One such embodiment involves providing a particle with a sharp "tip" at one end and a broader, nail-head-like tail at the other end, such as to enable partial penetration of the particle and, if desired, subsequent retraction of the particle. Such a particle can be retracted using, for example, a tape-like backing which can adhere to the particle's broader tail.

In another specific embodiment, the surface of the particles can be shaped such as to attract and/or accommodate molecular matter (substances of interest). Examples of such molecular matter include DNA, RNA, proteins, cell material, salts, sulfonamides, pharmaceutical substances, enzymes, viruses, and marker substances like upconverting phosphors. By shaping the surface of the subject particles to attract and/or accommodate such substances of interest, the subject particles can more effectively deliver this molecular matter to the inside of the target body. The particle can also be designed to enhance detachment of such substances during entry into the target material or after entry into the target material. For example, the molecular matter can detach under the effect of the prevailing force vectors.

In addition, the surfaces of the subject particles can be conditioned such as to more effectively attract and accommodate molecular matter. In specific embodiments, conditioning of the particle surface can encompass altering one or more of the following surface properties of the particle: topography; pH; electrochemical potential; van der Waals forces; surface energy; and other surface conditions. These surface conditions can cause the particle's surface to readily absorb and hold the payload substances, or to carry precipitated payloads and retain them with less holding force than the desorption or dissolution force is capable of exerting onto the payload. Accordingly, particle surface conditioning can help to assure delivery of the payload substances of interest to the interior cell plasma or other such target body, such as to enable its interaction with said body. Such interaction can include, for example, gene introgression or vaccination with the delivered genetic material.

After the particles have come to rest with respect to the target, for example when an externally applied magnetic field used for propelling the particles is shut off or mechanical or dynamic delivery is terminated, secondary interactions between the particle and body can be accomplished. For instance heating of the particle by activating a resonant circuit loop placed on the particle can trigger the release of material held by the particle, enhance the efficacy of materials released by the particle, and/or heat the target to affect the interaction between the particle and the target. Secondary interaction between the particle and the target can also be enabled by applying an external magnetic field for purposes of, for example, marking, tagging, retrieving, sorting, rotating, counting, and/or detecting the target material.

In order to protect the payloads against shear forces while penetrating the target site and its protective walls, the particles can be encapsulated together with their payloads. Such encapsulation can provide catalyst material for stimulating chemical interactions between payload and target material.

In a further embodiment, the subject particles can be coated by means routine in the art with substances of interest such as materials which attract viruses, bacteria, and/or other organisms or agents. Once attracted, these organisms or agents can be captured on the particle surface. These organisms or agents can then be held to the particles while the particles are, for example, magnetophoretically introduced into or extracted from the target site. These techniques are applicable in vivo and in situ. Accordingly, these techniques can be utilized for installing or removing these entities or other potential malefactors.

Advantageously, the subject particles can, in part due to their small size, shapes, and low surface energy or low coefficient of friction (for example, in an embodiment having a TEFLON coating), readily slip through muscle tissue or other body substances and thereby provide a means for deeply penetrating an entity, such as a human body, without surgery and without inflicting serious injury. The subject technique can be applied to an organ, cell, or other chemical or structural entity whose composition can be altered and remain altered by the presence of the substances of interest delivered to it, as well as the continued presence of the delivered particles until they are removed. The subject particles can initiate a permanent transformation of the consistency and condition of the target site so as to effectuate its healing or its replicative genetic transformation on account of the substances (the payloads) delivered by the carrier particles to the body, cell, pollen, or bioplasma present at the target site. The subject particles can be important elements in a magnetophoretic delivery system, allowing delivery of various substances of interest without the need for surgical invasion or using the blood stream to circulate medicinal substances in order to reach the target site.

The delivery of the subject particles to a target can also be used to initiate a temporary transformation or stimulation either with a payload or alternatively the particles by themselves. For example, they may be employed in order to trigger a cascade of events such as an immune response, a hypersensitive or systemically active resistance response, viral replication or movement, and/or fertilization with extranuclear or satellite genetic material, or particles themselves can be used to cause effects analogous to acupuncture.

Exposure of the subject particles to a preparatory magnetic field prior to executing delivery by magnetophoretic, mechanical, or dynamic means can be used to maintain dispersion, to direct the orientation of, and/or to temporarily immobilize said particles. In a specific embodiment, the subject particles can be coated in a dispersed, oriented, and immobilized state during exposure to a magnetic field. Further immobilization of the oriented, dispersed, and conditioned or coated particles in a matrix or with backing tape suited to the particle delivery method, can be utilized for stabilization of the particles in conjunction with, or in the absence of, a preparatory magnetic field.

Advantageously, the subject particles can be mass produced having various types, sizes, compositions, and features. The subject particles can be manufactured with precision using an apparatus for continuously creating, extracting, gathering, conditioning these particles to accept the substances for which they were designed. The coated particles can then be stored in a suitable medium such that they are ready for use when needed.

BRIEF DESCRIPTION OF THE DRAWINGS

The claim of this patent contains at least one drawing executed in color.

DETAILED DISCLOSURE OF THE INVENTION

The subject invention relates to a method and apparatus for the manufacture of magnetizable carrier particles, sometimes also referred to herein as "micromagnets" or "microparticles". In addition the subject invention pertains to particles having one or more of a variety of particle configurations and/or functional features. These particle configurations and/or functional features can be tailored to achieve one or more desired missions. The subject invention also pertains to a method and apparatus for the delivery of particles to target materials, in order to accomplish one or more of a variety of missions.

The subject invention pertains to particles which can be delivered or otherwise manipulated by a magnetophoretic particle delivery apparatus. These particles and associated treatment agents can thus be introduced into cellular targets such as microbial, plant, and/or animal cells and tissues comprised of these cells. The subject particles can be used to deliver substances that initiate "healing" or "genetic transformation," or for other purposes such as "marking" of the target material at the target site. Accordingly, the characteristics and associated properties of the subject particles can greatly impact the effectiveness of substance delivery and/or extraction.

Figure 23:
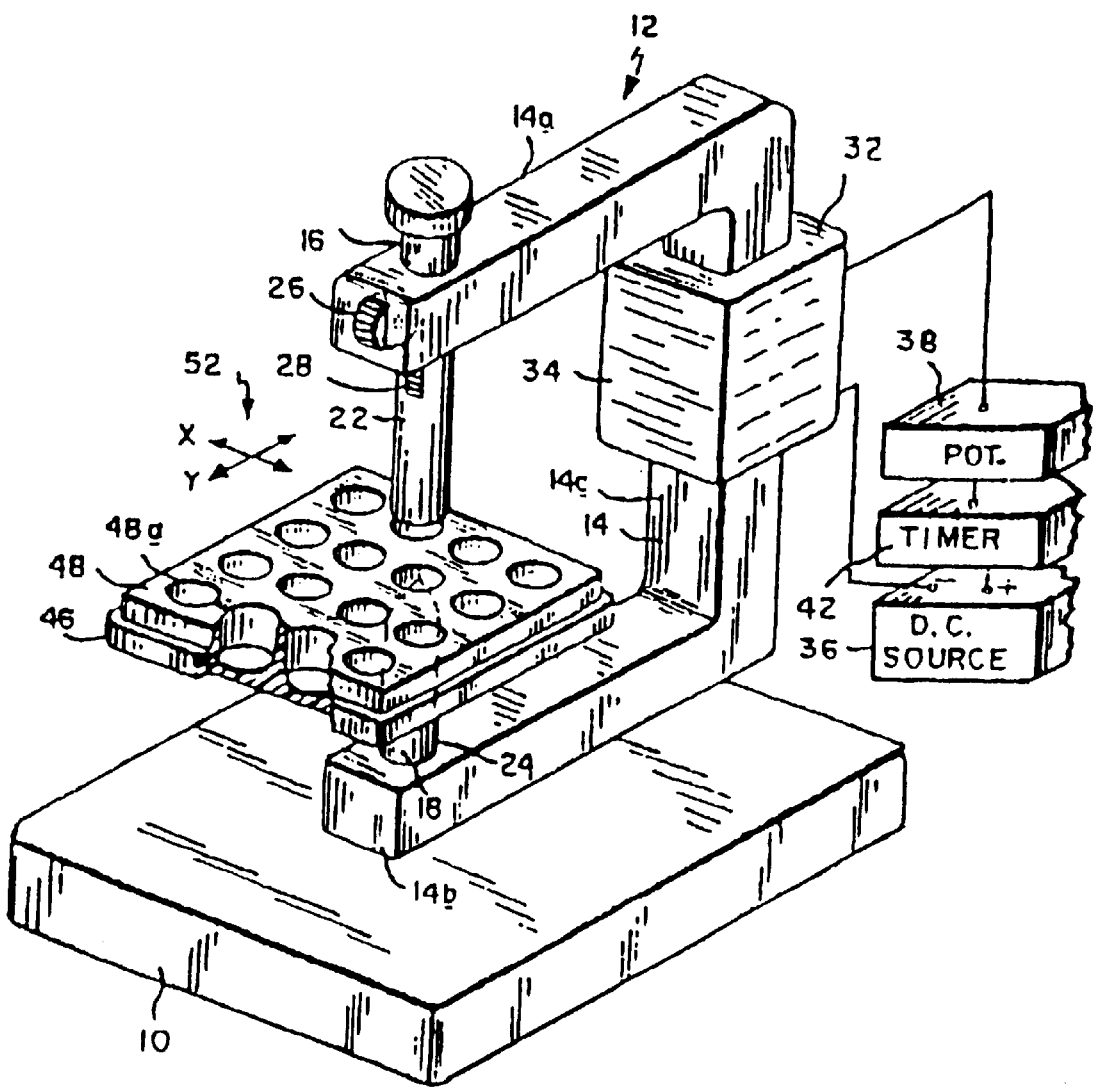
FIG. 23 is an isometric view of a magnetophoretic particle delivery apparatus with which the micromagnets of the subject invention can be used.
Figure 24:
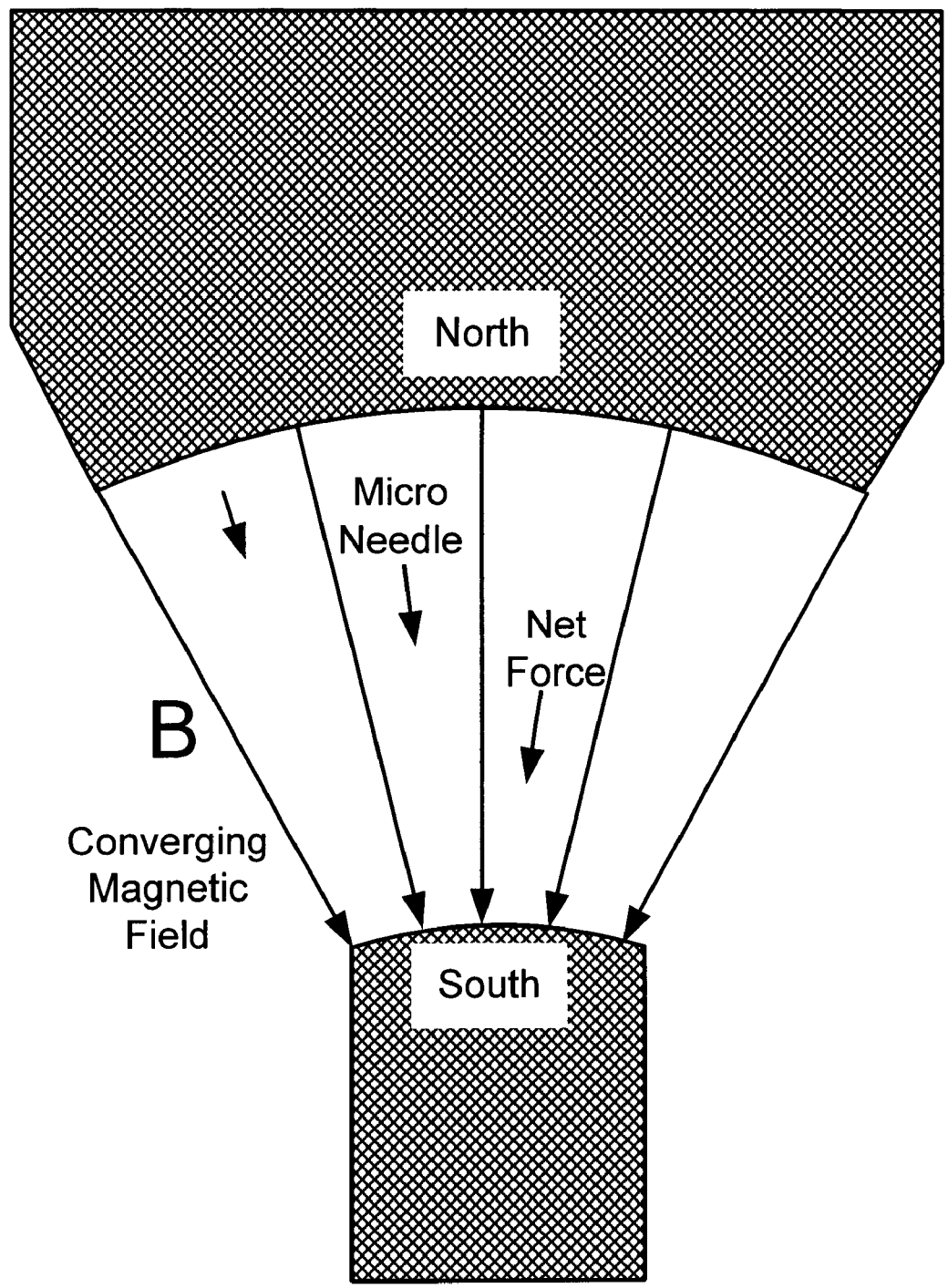
FIG. 24 depicts the force vectors on substantially acicular micromagnets traveling in a converging magnetic field, B.

Referring to FIG. 23, a magnetophoretic delivery apparatus is shown which can be utilized to deliver one or more of the subject particles. The delivery apparatus comprises a base 10 which supports a relatively large electromagnet shown generally at 12. Magnet 12 includes a generally C-shaped yoke 14 having parallel upper and lower arms 14a and 14b and a bridging portion 14c connecting corresponding ends of the two arms and extending generally perpendicular thereto. The lower arm 14b is mounted to base 10 by suitable means such as threaded fasteners (not shown). Preferably the yoke 14 is composed of a multiplicity of laminations.

A pair of coaxial vertical holes 16 and 18 extend through yoke arms 14a and 14b, respectively, adjacent to the free ends thereof Mounted in holes 16 and 18 are a pair of upper and lower pole pieces 22 and 24, respectively. The pole pieces are colinear and project toward one another leaving a gap between their adjacent ends. Preferably, at least one of the pole pieces, i.e., pole piece 22, is movable vertically relative to the yoke in order to adjust the size of the gap between the two pole pieces. Thus, in the illustrated apparatus, a thumb wheel 26 is rotatably mounted in the end of yoke arm 14a. The thumb wheel has teeth which engage the teeth of a rack 28 extending along pole piece 22 so that by rotating the thumb wheel, the pole piece can be moved up and down. Alternatively, pole piece 22 may have a threaded upper segment which engages corresponding threads in the hole 16 so that rotation of the pole piece causes it to move up and down relative to yoke 14 and pole piece 24. Various other mechanisms can be utilized for bringing pole pieces 22 and 24 toward, and away from, each other.

A bobbin 32 carrying an insulated wire coil 34 surrounds the yoke bridging portion 14c. One end of coil 34 is connected to the negative terminal of a DC source 36. The other end of the coil is connected to the positive terminal of that source by way of a potentiometer 38 and a timer 42. When pole 34 is energized, a very strong magnetic flux is induced in yoke 14 which flows across the gap between the pole pieces 22 and 24. The duration of that field may be controlled by timer 42 and the strength of the field may be varied by adjusting potentiometer 38.

The apparatus shown in FIG. 23 also includes a generally horizontal rack 46 for supporting a specimen holder or well plate 48 so that the holder is situated in the gap between the two pole pieces. The illustrated specimen holder 48 comprises a flat plate containing a plurality of shallow wells 48a arranged in columns and rows. Preferably, each of these wells 48 has a concave bottom wall. Preferably also, rack 46 is supported by base 10 by ways of a conventional X–Y positioner indicated generally at 52 which allows the indexing of rack 46 so that each of the wells 48a can be positioned on the common axis of the pole pieces 22 and 24.

While the present invention is intended to be used preferably with devices such as described above, use of a permanent magnet if sufficiently strong and of correct field geometry, or use of any other mechanical or dynamic means, can accomplish a similar effect for certain targets.

In certain situations, the subject particles are designed to penetrate target material. In order to accomplish this the particles must move and impact the target body, cell, pollen, or organ in such a way as to exert a sufficiently large pressure to breach any protective wall that may surround the target. This motion and resulting force on the target body can be generated by an appropriate magnetic apparatus, with the force defined as follows:

$$Force_{particle} = \frac{dB_{appl} \cdot B_{sat}}{dx \cdot \mu_0} \cdot Area_{cross\,sect} \cdot l$$

wherein $$\frac{dBappl}{dx}$$

is the applied magnetic flux difference across the particle length, Bsat is the saturation level of the particle matrix, and Area ·l is the volume of the particle.

Due to the field strength gradient that characterizes the converging, conical magnetic field of the magnetophoretic apparatus, the acicular and other magnetizable particles with a lengthwise dimension will move towards the target and exert pressure at the point of contact inversely proportional to the size of the contacting tip:

$$pressure_{tip} = \frac{Force}{Area_{cross\,sect}}$$

As an example, with a particle length of 50 $\mu$m and a needle cross section of 1 $\mu$m ×2 $\mu$m featuring a NiCo alloy with 8000 gauss saturation flux, when this particle is subjected to a field gradient of 5000 gauss/cm, then the force induced by the gradient will be:

$$F_{part} = \left(\frac{5000\ gauss}{cm}\right)\left[\frac{8000\ gauss}{4\pi \cdot 10^{-7}\frac{volt-sec}{amp \cdot m}}\right](2\ \mu m^2 \times 50\ \mu m)$$

Now, if the particle (micromagnet) has a sharp tip of 100×100 Angstrom≈$10^{-4}$ $\mu m^2$, then the $$= 3.2 \times 10^{-4} dyne = 3.2 \times 10^{-4} milligrams/particle\ (2\ \mu m^2\ cross\ section)$$

$$= 3.2 \times 10^{-9} \frac{volt \cdot sec \cdot amp}{m} = 3.2 \times 10^{-9}\ Newton$$

pressure will increase to $$P_{tip} = 2 \cdot \frac{3.3 \cdot 10^{-4}}{10^{-4}} mg/\mu m^2 \cong 6.6\ kp/\mu m^2\ equivalent$$

As is evident from these calculations, the sharpness of the tip determines the pressure on the target sample wall which, once its resistance is overcome by the particle pressure, will yield and allow penetration by the particle into the target body. Thus, with 3.3 milligram/2 $\mu m^2$ blunt tips the pressures that can be exerted against resisting obstacles such as pollen, cells with walls, meristems, body skin, organs, live bone, and other substances can be, for example:

Tip 1.0 $\mu m^2$=6.6 kp/$\mu m^2$ 0.1 $\mu m^2$=66 kp/$\mu m^2$ 0.01 $\mu m^2$=660 kp/$\mu m^2$

These pressures can be formidable if attention is paid to the sharpness of the particle tip. With the aid of a magnetophoretic or other apparatus, it is possible with the particles of this invention to penetrate hard substances such as microscopically hard pollen and deliver chemical substances such as DNA, enzymes, and others. It should be noted that when the tip of the needle begins to exert a force onto the skin surface of the target body, said body will try to resist the penetration by forming lateral forces whose magnitudes are nearly infinite as is evident from the parallelogram of forces. Thus, even the slightest scratch caused by the sharp needle tip will cause the rupture of the skin due to said lateral force.

Figure 1:
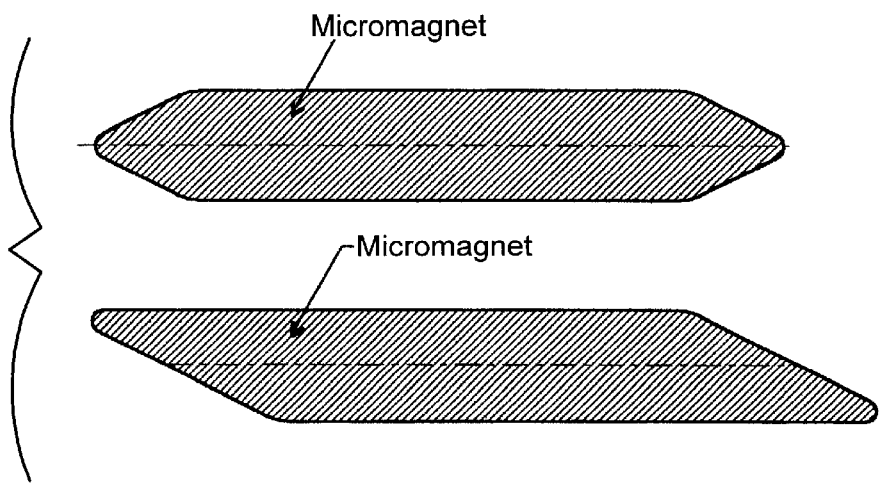
FIGS. 1a and 1b show typical acicular microparticles according to the invention whose outsides can be coated with "payload" materials.
Figure 2:
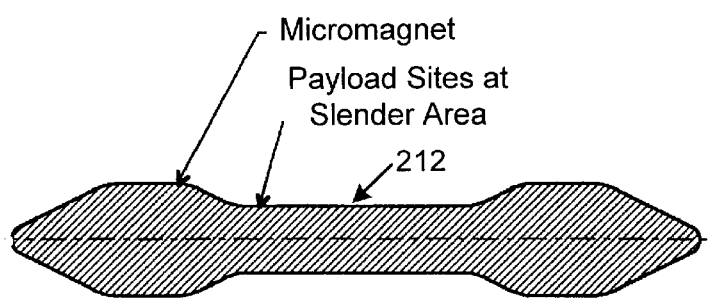
FIG. 2 shows an alternative, slenderized design for payload accommodation with bulkier material.
Figure 3:
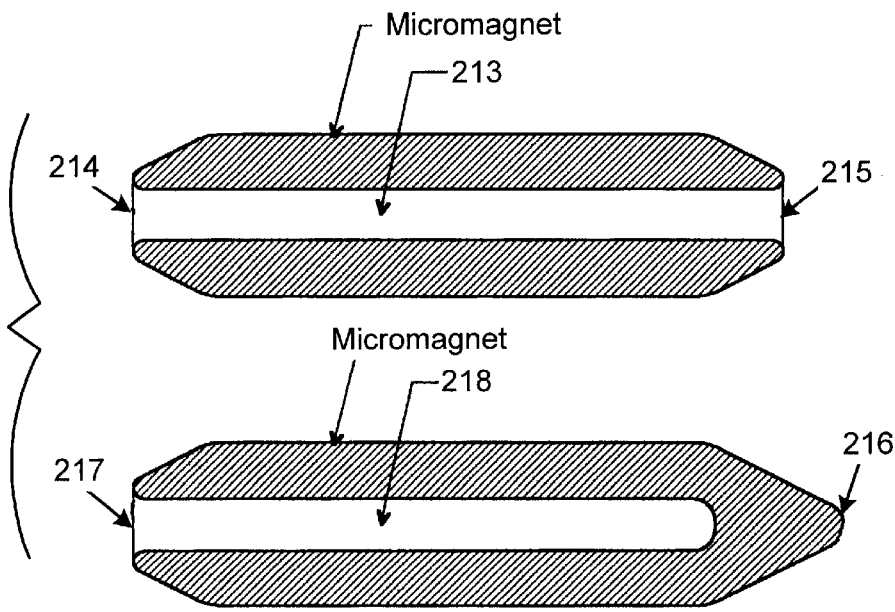
FIGS. 3a and 3b depict longitudinal cross-sections of hollow particles of the subject invention; and also are an accurate depiction of surface views of grooved particles according to the invention.
Figure 4:
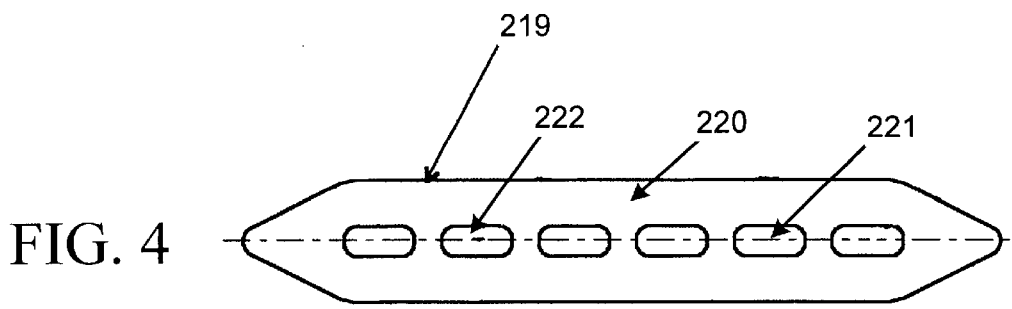
FIG. 4 depicts a dissolvable microparticle configuration, having a plurality of magnetizable particles embedded therein.
Figure 5:
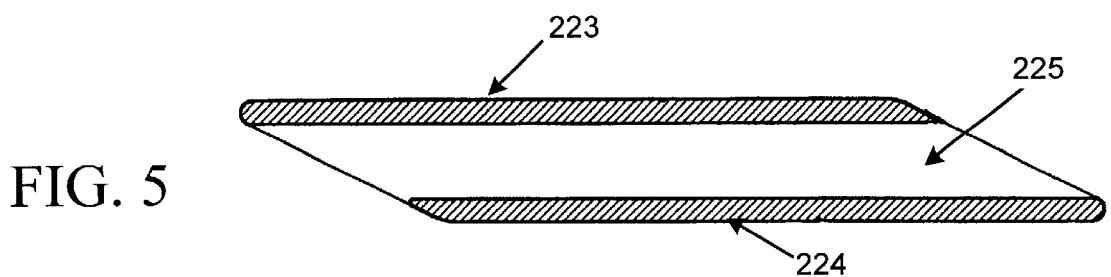
FIG. 5 shows a particle having an electrostatic groove which can be charged electrostatically to hold a polynucleotide in stretched-out form and release the polynucleotide as the charge decays.
Figure 6:
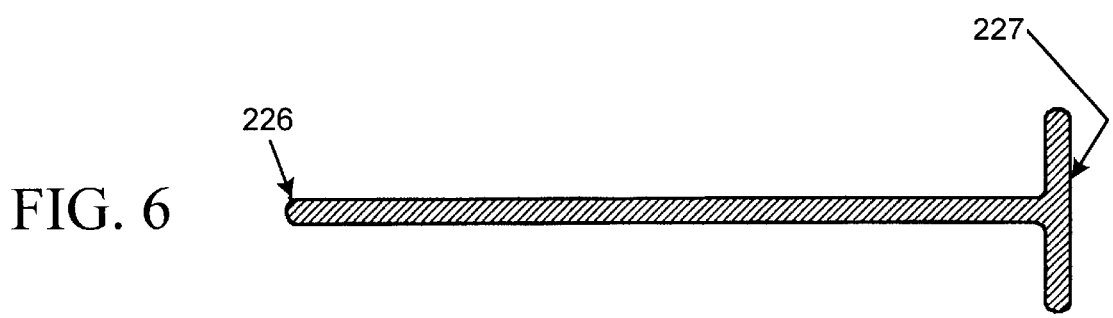
FIG. 6 depicts a particle having a sharp "tip" or multiple tips at one end and a broader nail head-like tail at the other end.
Figure 7:
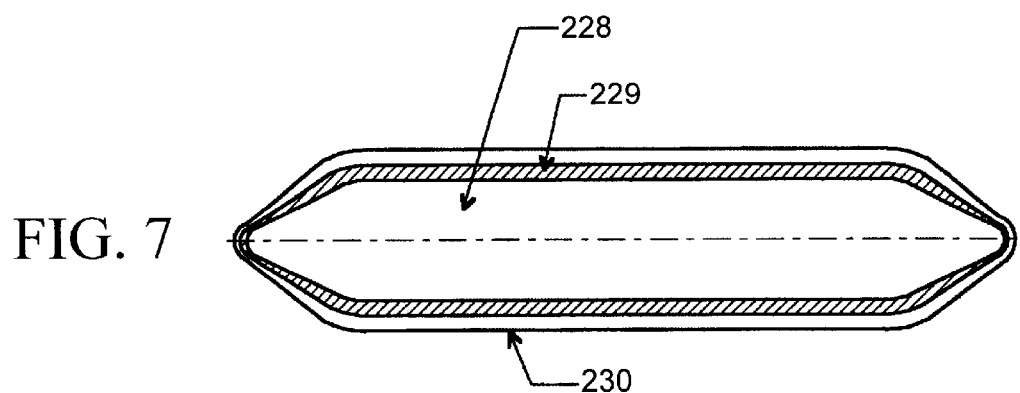
FIG. 7 depicts a longitudinal cross-section of a multilayered particle having a core micromagnet, an electrical insulation encapsulation, and an external payload whose dissolution in the target body can be "timed".
Figure 8:
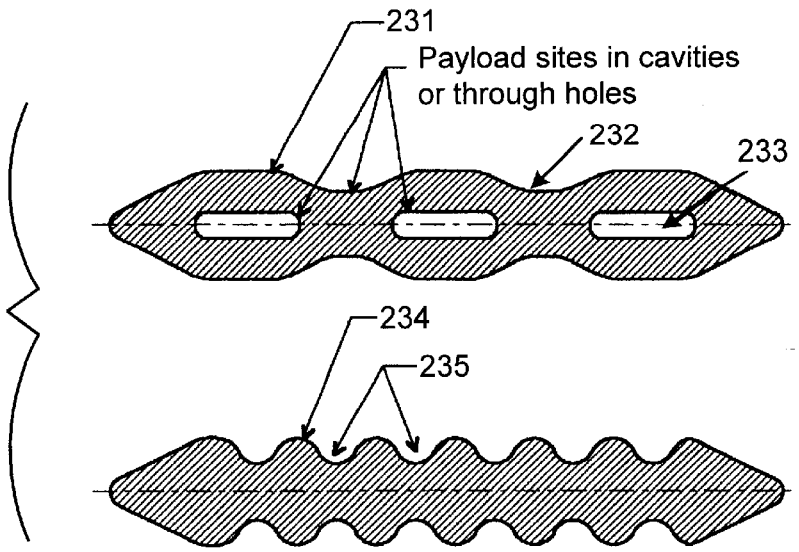
FIGS. 8a and 8b show particles having an exterior surface which is articulated with surface undulations to enable the payload to adsorb itself to the recesses with increased holding power.

FIGS. 1–11 and 14–21 illustrate various embodiments of the subject invention. FIG. 2 depicts a magnetizable microparticle having a modified geometry including payload site 12, which is a slender area on the microparticle of reduced diameter. FIGS. 3a and 3b depict additional microparticles having altered geometries. FIG. 3a provides equally accurate depictions of two alternate geometries; it can be viewed as a longitudinal cross-section of a hollow microparticle disclosing a channel 13 passing longitudinally through the microparticle and having openings 14 and 15 at each end; alternatively, it depicts a side view of a microparticle having a groove 13 running longitudinally the entire length of the microparticle. Similarly, FIG. 3b can be viewed as depicting either a longitudinal cross-section of a microparticle having a closed end 16, an open end 17, and a hollow chamber 18 substantially longitudinally centrally located within the particle; alternatively, this figure depicts a side perspective view of a microparticle having a longitudinal groove 18 extending from one end 17 along more than half of the particle's length. FIG. 4 depicts a dissolvable magnetizable microparticle 19, comprising microscopic magnetizable particles represented at 21 and 22, embedded within a solidified, water-dissolvable binder 20. FIG. 5 depicts a microparticle having an electrostatic groove 25 defined by raised sidewalls 23 and 24 running the length of the microparticle. As shown in FIG. 6, magnetizable microparticles having a sharp tip 26 (or multiple sharp tips) can be configured to extend from a broader nailhead like tail 27. FIG. 7 depicts a microparticle 28 coated with a payload substance of interest 29 which itself is coated with a dissolvable skin 30. The sequential layers of payload and dissolvable external skin can be applied by means well known in the art, and render delivery of the payload to internal targets more efficient under certain circumstances. In FIG. 8a, micromagnet 31 is depicted with a geometry presenting payload sites in slender areas or cavities 32 as well as having payload holes 33 extending through the microparticle for greater duration of payload carrying capacity. FIG. 8b shows an alternative geometry for carrying payload depicting micromagnet 34 with a plurality of payload sites 35 resulting from "scalloped" edges along the length of the microparticle. In this embodiment, the approximate diameter of the payload sites created by the scalloped edges ranges from approximately 130 nm to approximately 500 nm. FIG. 10 shows microparticle 39 with a payload carrier hole 40, wherein the substance of interest to be carried with the microparticle is a radioactive tracer. As will be apparent to one skilled in the art, these and other unique geometries can be created by patterned perforations in a template, or by other means such as mechanical manipulation on a microscopic scale.

The substantially acicular microparticles of the subject invention can be optimized for maximum functionality. The magnetic responsivity of the subject particles can be maximized for a particular application by choosing their material composition as well as their geometry. Different applications can utilize particles of different geometries. The various geometries of microparticle, for example as depicted in FIGS. 2, 3, 5, 6, 8, 10, and 11, can be readily obtained according to the manufacturing methods described herein, and by use of templates having designed perforations corresponding to the desired geometric configuration. For purposes of mass production, it may be preferred to alter the geometry of the particles rather than the material composition. However, using a material having a different magnetic responsivity can also accomplish the desired change in particle properties. For example, rare earth magnetic materials, or multi-material composites can be utilized when a particle which is dissolvable in the target body is needed. In general, for agroscience applications, the length of the particles will be very small, and for animal or human body applications and applications requiring many centimeters of travel length, the dimensions can be as much as about 100 times larger. Table 1 provides examples of preferred particle dimensions which can be used according to the subject invention.

TABLE 1

| Particle Length | Particle Cross Section | Applications |
| --- | --- | --- |
| 10 μm | 1 × 1 μm | Pollen, Egg, Cell treatment |
| 1000 μm | 100 × 100 μm | Tumor treatment |

Listed in Table 2 are a number of magnetizable materials which are available, and can be utilized to produce the subject particles. Other materials having magnetic properties can also be used. Preferably, materials having low coercivity can be used to produce the subject particles.

TABLE 2

| Material | Saturation Induction (gauss) | Coercive Force (Oe) |
| --- | --- | --- |
| $Fe_3O_4$ | 6,000 | |
| Fe | 21,580 | 1 |
| $MnFe_2O_4$ | 4,900 | |
| Supermalloy | 7,900 | 0.004 |
| Permalloy | 10,800 | 0.05 |
| Nickel | 6,100 | |
| Fe(60%)Co(40%) | 24,500 | |
| Cobalt | 17,900 | |
| Fe(50%)Ni(50%) | 17,900 | |

Figure 12:
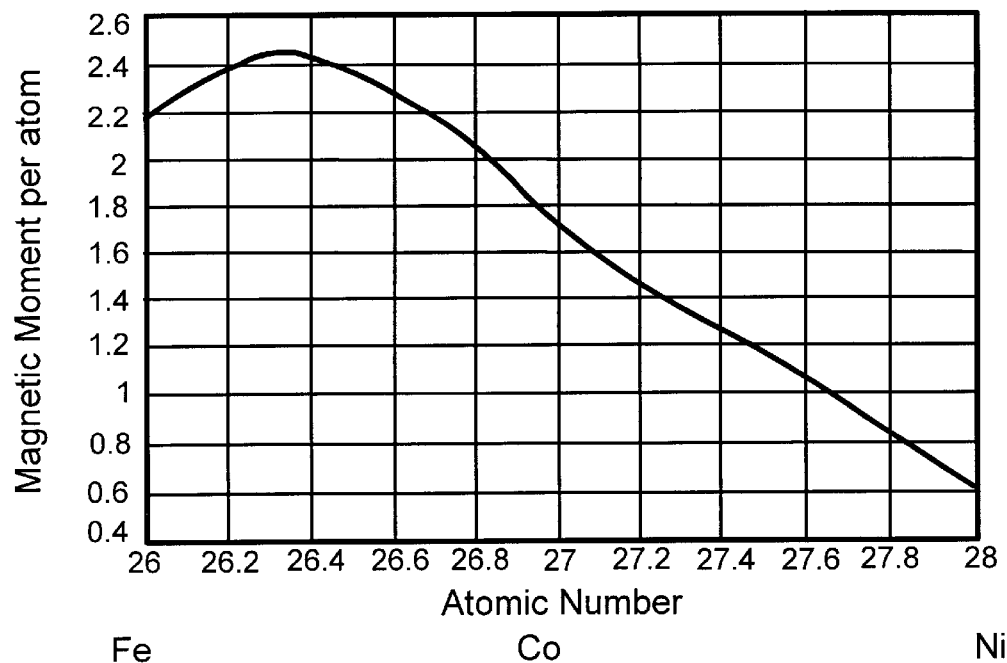
FIG. 12 illustrates magnetic moments in Bohr Magnetrons per atom for certain alloys.

As shown in FIG. 12, alloys of two of these materials, namely NiCo and FeCo can be made to show identical magnetic properties as a result of matching electron vacancies in the D-shell of the atomic structure.

The subject invention also relates to the preparatory orientation of the subject particles by exposure to a magnetic field prior to executing delivery by magnetophoretic, as well as by mechanical or dynamic means. This orientation can be fixed for the duration of exposure to the magnetic field and/or subsequently maintained by preparation of a carrier "ribbon" which can adhere to the tail ends of the oriented particles.

Figure 13:
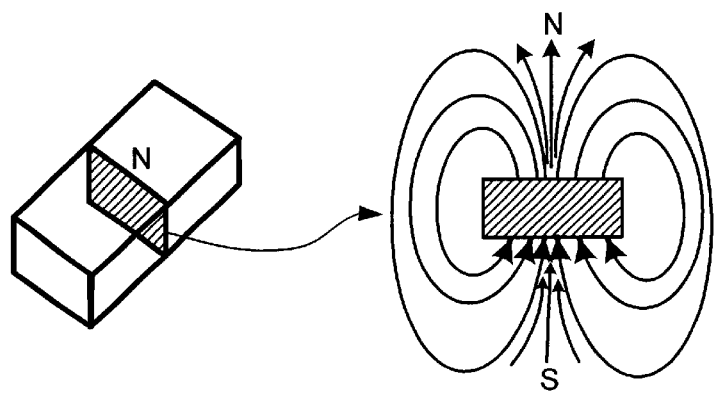
FIG. 13 illustrates the generally central, vertical field lines produced by bar magnets.
Figure 14:
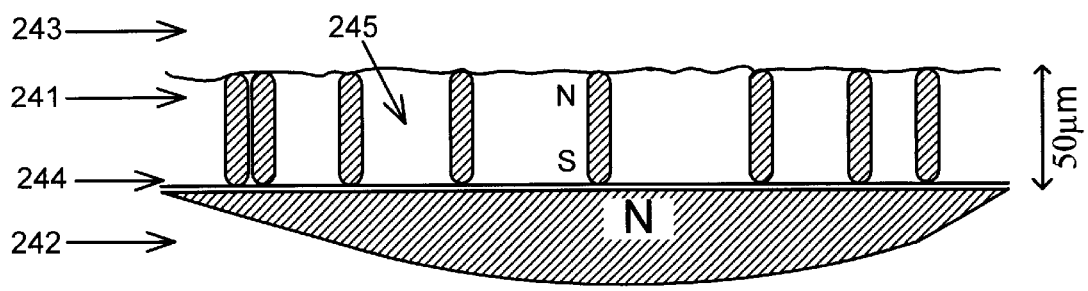
FIG. 14 illustrates stationary micromagnets aligned above a magnet in accordance with one embodiment of the subject invention.

Referring to FIG. 13, bar magnets generate central, vertical field lines due to N/S configuration. Referring to FIG. 14, monolayers of dispersed, perpendicularly and vertically oriented micromagnet particles 41 can be produced with the assistance of at least one bar magnet 42 to orient the particles. If desired, a parallel magnet can be positioned at 43 to assist in maintenance of microparticle orientation. Microparticles can then remain dispersed throughout any subsequent coating process, eliminating the need for vortexing or agitation during coating. Also, coated micromagnets can remain stationary during the rinsing phase (if needed) and are easily recovered from precipitation solution, eliminating the need for centrifugation. This can be referred to as "stationary coating". Micromagnets can also be oriented and/or coated on the top pole piece of the magnetophoretic device itself.

Stationary coating, in which the micromagnets are not shaken or vortexed during application of DNA, can be performed with the micromagnets 41 immobilized and vertically and/or near-vertically oriented on central field lines of a permanent bar magnet 42 (see FIG. 14) with no apparent loss of coating efficiency as determined by YOYO-1 (Molecular Probes, Eugene Oreg.) staining (referring to FIG. 15). This method does not require any agitation beyond that which occurs during pipetting as the established precipitation reagents of spermidine (30 mM), and calcium chloride (0.2 M) are added to the micromagnets (commonly 0.01% w/v in water) bathed in DNA (2 to 10 microgram).

Oriented, dispersed, and conditioned/coated particles can then be further immobilized in a matrix or carrier "ribbon"

suited to the particle delivery method, for stabilization of the particles in the absence of a preparatory magnetic field. Magnetic particles 41 in dispersant 45 (the "microparticle solution") are dispersed onto a plastic support sheet 44 with optional mu metal for pattern masking (for precise particle positioning, for example along vertical field lines). The plastic can be lowered vertically on top of the bar magnet 42. The particles can then align with the available field lines such as the vertical field. Chain formation can be avoided by limiting the volume of the microparticle solution relative to the coating zone on the plastic sheet, such that the liquid's surface tension is stronger than the magnetic forces imposed on the particles during particle-to-particle interaction. Also, a sandwich can be made if desired with a second magnet 43 having field lines parallel to the field lines of the bottom bar. A further example is such oriented, dispersed and conditioned micromagnets being stored in frozen discs or in solidified alginate, agar, agarose, or Phytagel blocks. Such storage can be long term, including for DNA-coated particles, if using frozen discs, for example. Frozen discs are adhered to the top, broad pole piece of a magnetophoretic device (using a drop of glycerol, for example) or placed directly in contact with target tissue before the pole pieces are brought close together. The magnetophoretic device may be turned on during or immediately after the thawing process. As the frozen liquid thaws, particles are released. Observations show that only a small amount of DNA comes off the microcarriers during the freeze-thaw process.

Acicular, needle-like magnetizable microparticles made in accordance with the subject invention that are aligned in a monolayer can also be controllably exposed to an electric field whereby said uniformly long microparticles conduct electricity to the particle tips, thereby creating an electrostatic field at said microparticle tips, and being able to impose electrical fields within the target specimen. This is useful to aid in the molecular interaction between the payload and the substance to be treated.

Figure 15A:
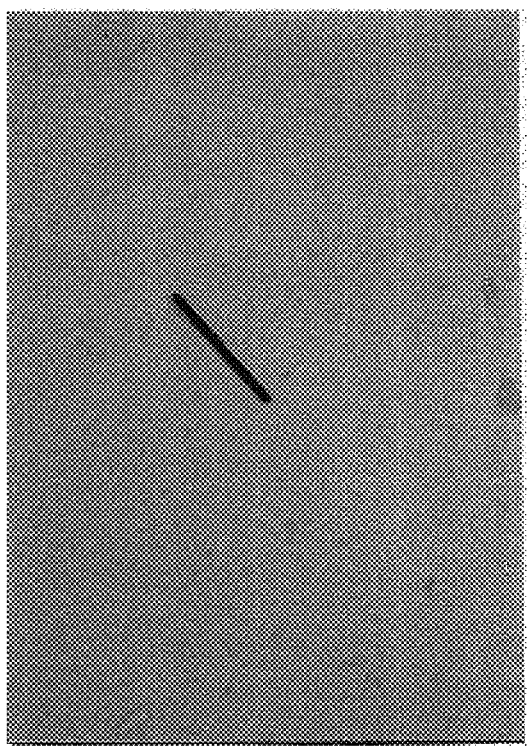
FIG. 15a is a bright field view of a nickel-cobalt micromagnet, 50 micron length, coated with plasmid DNA fluorescently labeled with yoyo-1 dye using a stationary coating method (400×).
Figure 15B:
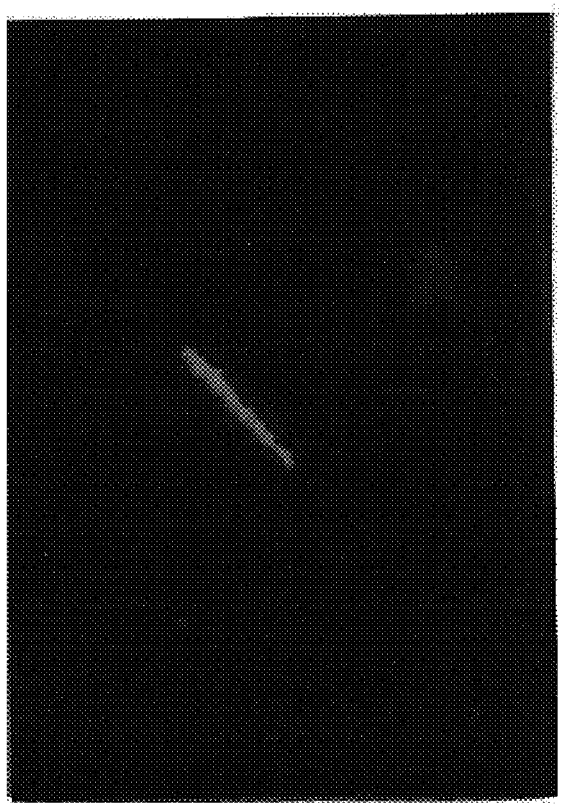
FIG. 15b is the same micromagnet viewed under UV light of 491/509 wavelength to reveal the DNA on the particle surface by fluorescing green.
Figure 16:
FIG. 16 depicts transient expression of the GUS reporter gene producing blue color in otherwise colorless Black Mexican Sweet maize cell suspension after magnetophoresis with DNA-coated nickel-cobalt micromagnets of 50 micron length (200×).
Figure 17:
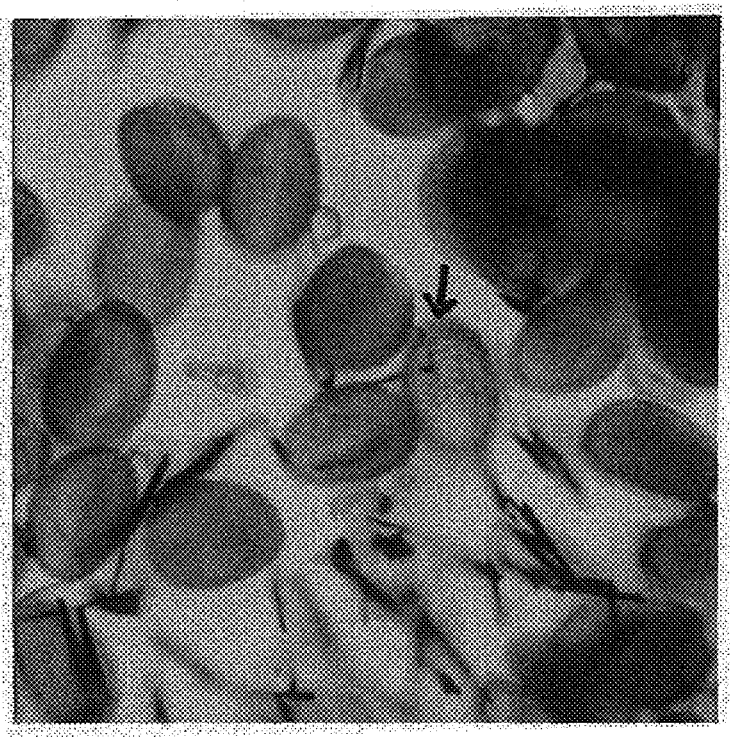
FIG. 17 shows a single nickel-cobalt 50 micron micromagnet spearing a pollen grain as indicated by arrow (particle is oriented from 12 o'clock to 6 o'clock through the grain) (200×).
Figure 18:
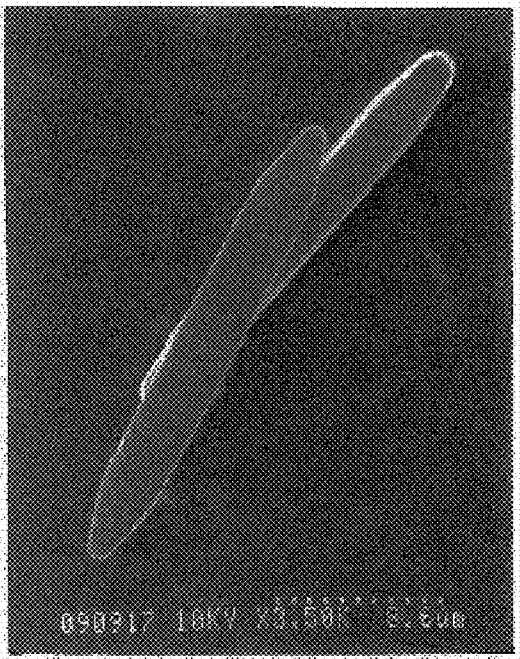
FIG. 18 shows one embodiment of the micromagnets of the subject invention. At the bottom left is the tapered tip of a nickel-cobalt micromagnet with dimensions of 0.5 micron tip, 1.4 to 2.6 micron thick, 25 micron length, 3.3 micron wide (3500×).
Figure 19:
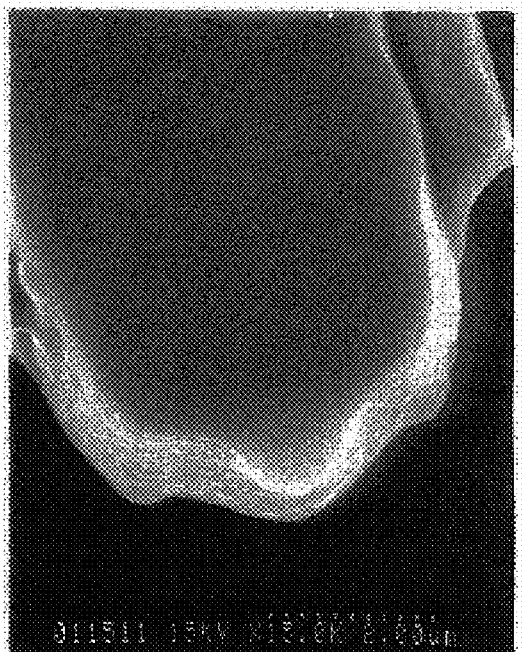
FIG. 19 depicts an alternative embodiment of the subject invention having a variation in tip geometry (15000×).
Figure 20:
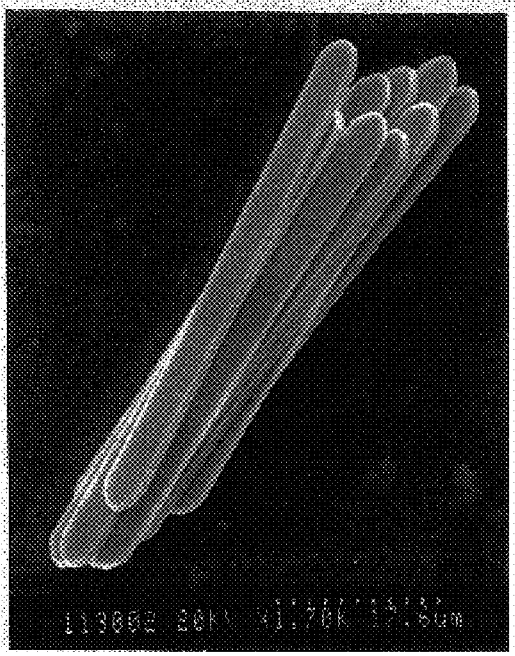
FIG. 20 depicts yet another embodiment of the subject invention, typical acicular micromagnets, having approximately 50 micron length.
Figure 21:
FIG. 21 is a further magnified view of micromagnets as in FIG. 20, showing alternating layers of magnetizable metal which form the micromagnets.

Coating of the subject particles with "payload" can be accomplished. Using DNA as an example, an established precipitation mix of spermidine and calcium chloride can be utilized as described above. A carrier matrix can be applied around the micromagnets for embedding. (See FIG. 14). The plastic support ensemble can then be removed from the bar magnet and the ribbon of coated micromagnets can then be used or stored. Examples of stationary-coated micromagnets are shown in FIGS. 15a and 15b. FIG. 15a is a bright field view of a nickel-cobalt micromagnet, 50 micron length, coated with plasmid DNA fluorescently labeled with yoyo-1 dye (400×). FIG. 15b is the same micromagnet viewed under UV light of 491/509 wavelength to reveal the DNA on the particle surface by fluorescing green.

Alternatively, use of a thin magnetic strip attached to a macrocarrier of magnetic microparticles can allow "stationary coating" as well as continued maintenance after coating of particles in a dispersed, oriented, and immobilized state in air, rather than in a support matrix. Such an arrangement can then be ready for immediate use in certain delivery systems such as in the BioRad PDS1000.

Coating of micromagnets with nucleic acids can be accomplished in the absence of polyamines and salts. Exposure of nickel-cobalt particles to DNA in solution results in adherence of DNA to the particles. This is enhanced by spotting (pre-coating) the micromagnets with glass or HMDS. Alternatively pre-coatings of gold or tantalum may be used to enhance payload loading.

"Conditioning" or coating (or spotting) of the micromagnet surface with silica, the non-ionic polymer polysorbate 80, or carboxyl (COOH) groups can facilitate attachment of affinity ligands for virus or protein entrapment, either for their delivery to or their retrieval from targets. Coating by the process of silanization using organosilanes, as is known in the art, similarly permits coupling to affinity adsorbents for substance delivery or retrieval. Conditioning of the micromagnets with hexamethyl disiloxane, HMDS, applied through a vapor phase and by conventional means as in integrated circuit technology, allows direct attachment of organic payloads. Protein complexes including viruses can also adhere to the micromagnets following precipitation steps as is known in the art. For example, virus can be precipitated by isoelectric point or by saturation of ammonium sulfate as described in Matthews, 1991. Proteins of interest for conditioning of micromagnets also include receptors and antibodies.

Proteins or antigens are commonly prepared using histidine tags. Since histidine has a strong affinity for nickel, the nickel-cobalt micromagnets can serve as excellent tethers for his-tagged payloads. Protein tethered in this fashion is immunoreactive such that desorption is unnecessary.

Conditioning with TEFLON allows the micromagnet to be free of payload as it traverses several tissues or cell layers to the target site. Such protective coatings can assure long-term stability of the micromagnets, including in the target material.

Use of selective coatings, such as attachment of antibodies or hybridizing DNA probes, allows for detection of viruses, bacteria, proteins, or mycoplasmas, and for their retrieval and extraction. Since all viruses have a charge, and since there are monoclonal antibodies for major viruses, viruses can be attracted to the subject micromagnets. Thus, instead of using a stationary column for virus purification, the subject invention can be used as a mobile scavenger system if delivered through tissues or into cells using magnetophoresis. Other scavenging systems employ iron oxides or cementite as submicron particles that are syringe-injected into the blood stream.

The micromagnets of this invention are distinct in composition, geometry and manufacture from magnetic beads commonly used in affinity purification of proteins, nucleic acids, microorganisms and cells. Magnetic beads are prefabricated magnetic particles containing iron oxides, generally magnetite, often sub-micron in size and with no dominant lengthwise dimension in distinct contrast to the subject invention. Methods of manufacture of such magnetic beads are described, for example, in U.S. Pat. No. 4,554,088 issued to Whitehead et al. and references therein. The subject invention is distinct from colloidal particles notably from ferrofluids which generally encompass particles less than 0.03 microns in size and whose manufacture is described in U.S. Pat. No. 5,698,271 to Liberti et al. and references therein.

The subject invention is further distinguished from other magnetizable microparticles in that the subject invention is designed for use with a magnetophoretic particle delivery apparatus, permanent magnets, or other magneto-mechanical systems. Referring to FIG. 24, microparticles of the subject invention with the predominantly lengthwise dimension act as magnetic dipoles in a non-uniform converging field and thereby can move in a field gradient with a predictable force and pressure.

Furthermore, the method of manufacture of the subject invention is distinct from manufacturing extremely small iron-magnetic particles, generally iron oxides or cementite ($Fe_3C$) alloys of activated carbon with metallic iron, that are produced by fine grinding, vacuum deposition or chemical precipitation as is known in the art.

One use out of many for the subject micromagnets is delivery of drugs in humans and animals. Prior art uses microbeads or microspheres and are typically magnetically localized in capillary beds by a permanent magnet or by their size following intravascular administration. U.S. Pat. No. 4,345,588 of Widder et al. reviews a variety of magnetic iron oxides ranging in size from 300 Angstroms for $Fe_3O_4$ powders and colloidal suspensions to 1 to 5 micron diameter spherical microbeads. The magnetic responsiveness of the subject invention, by virtue of their composition and linear, microscale geometries, allow them to cross artery or other cell walls under influence of magnetophoresis in a focused path, thereby permitting a substantial amount of carrier particles to be delivered. These same features distinguish them from other magnetic microparticles of iron oxides or iron-carbon alloy used in medical applications such as reviewed in Allen et al., 1997.

Figure 9:
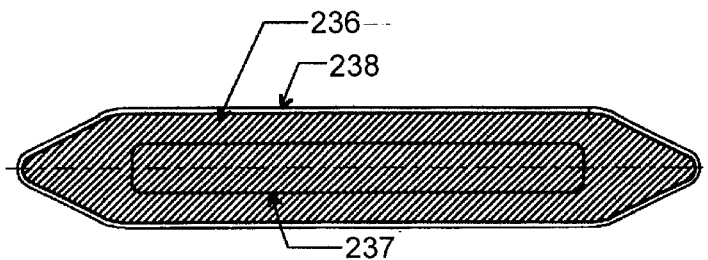
FIG. 9 depicts a particle, made of magnetizable or paramagnetic material, having an electronic circuit which can be brought into electrical resonance by a precise electromagnetic signal beamed onto the particle. This particle is coated with an electrical insulation material such as $SiO_2$ or $Si_3N_4$.
Figure 10:
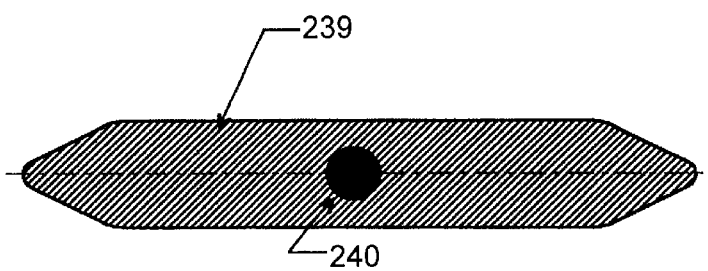
FIG. 10 shows a particle incorporating a radioactive tracer substance to enable location determination via radiometric sensing.
Figure 11:
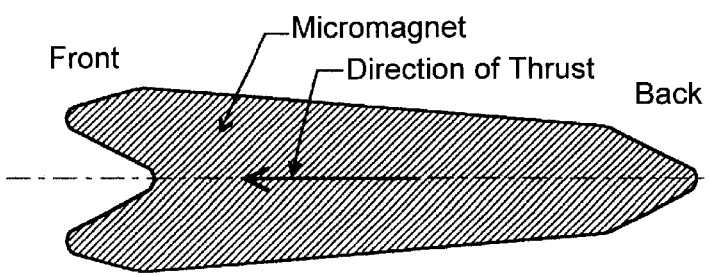
FIG. 11 shows a particle having an asymmetry of mass such that the particle is heavier on one end than on the other.

Microparticles of the embodiment depicted in FIG. 9 are particularly preferred for applications where, for example, microwave induced heating is desired, such as, for example, the killing of targeted cancer cells.

In a specific embodiment, nickel-cobalt micromagnets ranging in length from 10 microns to 100 microns can be inserted by magnetophoresis into a variety of animal and plant tissues including but not limited to plant cells (refer to FIG. 16), apices, pollen (refer to FIG. 17), leaves, trichomes, as well as into cultured human breast cancer cells and dissected bovine liver. In a further embodiment, nickel-cobalt micromagnets similarly ranging in length from 10 microns to 100 microns can magnetophoretically deliver DNA payload into target tissues with the subsequent expression of the exogenous DNA (refer to FIG. 16 for an example).

The magnetophoretic particle delivery can be implemented subsequent to mechanical injection of organs and tissues with magnetizable particles. This sequence of events can assure that a multiplicity of particles are present in a particular region prior to subsequent convergence on a specific target.

In a specific embodiment, Arabidopsis ovaries (siliques) are physically injected with magnetizable particles not to exceed 10 micron in length. These ovaries are then placed proximal to a pole of a magnet with converging field lines for directed motion of the particles into eggs, egg sac, or ovules.

In a specific embodiment, the side grooves (FIG. 21) of the layered metals and the specific geometries such as the slenderized designs of FIG. 2, and the hollow, grooved or cavitated designs of FIGS. 3, 5, 8, and 10, for example, enable the micromagnets to serve as carriers of large DNA fragments (>50 Kb) to assist in transformations using large genes, chromosomal segments, and multiple genes comprising, for example, elements of metabolic pathways; and to assist in map-based gene cloning using YACs or BACs (yeast or bacterial artificial chromosomes), for example. The micromagnet grooves and slenderized designs provide high surface area to accommodate such large DNA fragments and to sequester the payload and thus minimize DNA shear upon impact with the target.

As carriers of genetic material (for example, DNA, RNA, or DNA-RNA chimeras), which encode a therapeutic product or are themselves therapeutic, the micromagnets serve as agents of gene and gene-repair therapy and vaccine administration. In a specific embodiment, gene therapy for insulin-dependent diabetes mellitus is administered by coating with alleles of genes in the major histocompatibility region encoding resistance to disease per Maulik and Patel, 1997.

In a specific embodiment, genetic modification of fish is implemented by coating micromagnets with gene coding or regulatory sequences or their alleles such as for coloration or muscle growth modification followed by insertion into fish eggs. A further specific embodiment is in genetic vaccines against malaria administered epidermally to stimulate Langerhans cells, with or without an initial protein booster that may also be delivered via micromagnets.

Desorption of nucleic acids from coated micromagnets proceeds in a curvilinear fashion in aqueous solution as might be found in cytoplasm. In water, for example, radioactively labeled DNA desorbs by about 25% off nickel-cobalt particles in the first 20 minutes at room temperature after chemical adsorption.

In a specific embodiment, the subject apparatus and particles can be utilized for magnetic tagging or marking of cells and other target tissue.

Enrichment by magnetic means of cells that are magnetically tagged or marked following magnetophoresis using the micromagnets of the subject invention can include "static selection," whereby tagged cells are tethered in place by an external magnetic field such as a quarter-inch neodymium rod while the non-tagged cells are removed by gravity, for example, by tilting the container. Enrichment also includes "active sorting," whereby tagged cells are actively segregated by mobilization away from non-tagged cells using an externally applied magnetic field such as a quarter-inch neodymium magnet. This has been demonstrated using pollen and embryos that were magnetophoretically treated with nickel-cobalt micromagnets of 10, 25, and 50 microns in length and sorted using a quarter-inch neodymium rod. The same has been demonstrated using cell suspensions of maize, and can be easily adapted to animal systems like eggs of fish, for example, or will be readily appreciated by the skilled artisan.

Magnetic enrichment for newly magnetized cells or tissue, or subcellular structures, can supplement or even replace use of other selection means, such as use of antibiotics and herbicides and related genes for resistance to these selection agents in plant systems. The method of the present invention thereby greatly improves the efficiency of selection over the state of the art.

The subject invention is thus distinct from selection of cells using immunomagnetic means as described by Tibbe et al., 1999, which concerns use of submicron ferrofluids, without regard for the particle's lengthwise dimension as important, for the magnetic labeling of the cells prior to sorting.

In the subject invention, magnetic enrichment is enhanced by doping tagged cells with additional external micromagnets to increase overall magnetic responsiveness of the tagged cells due to increased magnetic material. This is implemented using free-floating micromagnets that become attached to cells already penetrated by micromagnets upon exposure to a weak magnetic field. The externally applied micromagnets can be additionally labeled by fluorescent dyes, as is known in the art, to distinguish subsets of separately treated cells in a pooled population, such as may be useful for bringing together unlike fusion partners, for example.

Cells or tissues embedded with micromagnets can be visualized by diagnostic imaging methods such as X-ray.

Description of the Manufacturing Methods

As shown in FIGS. 1–11 above, a number of geometries are preferred for optimizing micromagnets that suit various uses. Their length may vary from typically 2 $\mu$m to 100 $\mu$m; 500 $\mu$m; 1,000 $\mu$m; or more. They are preferably substantially acicular, and within any particular assemblage of microparticles they preferably are relatively uniform in length-to-width ratio, although this ratio may vary widely depending on the intended purpose and at the desire of the practitioner. The length-to-width ratio of the acicular particles can be as low as about 4:1, to as great as about 500:1 depending on the intended use; is preferably from about 5:1 to as great as about 300:1; still more preferably from about 7:1 to about 200:1; and for most uses is generally preferred to be from about 10:1 to as great as about 25:1. Whatever length-to-width ratio is chosen for a particular project or application, it is generally preferred that all of the acicular particles be of a similar dimension so as to constitute a generally uniform and homogenous assemblage whereby each of the magnetizable particles behaves similarly to the others. At the ends of the magnetizable acicular particles the width can be reduced, tapering to form points if desired, which generally could be as small as about 0.5 μm or even to about 0.1 μm in width. Particles may have an asymmetry of mass while retaining a predominant lengthwise dimension.

Magnetizable compounds useful for manufacturing the subject particles include nickel, supermalloy, permalloy, cobalt, iron, and preferably are combinations of iron-nickel, nickel-cobalt, or iron-cobalt. More preferable are alloys, with Fe-Ni alloys substituting for both Ni-Co or Co-Fe alloys depending on such factors as cost or ease of fabrication. Generally, the most preferable composition is one with a peak saturation magnetization, such as Co-Fe in a 40%:60% Co:Fe proportion. If desired, other non-magnetic compounds may be used in combination with the magnetic compounds mentioned above, and manufactured according to teachings herein, for example, providing a gold or silica glass "skin" over a Co-Fe core. Also, the geometric features can be varied to optimally enable the storage of reactive substances on the surface or within the structure.

EXAMPLE 1

Manufacturing Method 1—Metallic Vaporization and Deposition

A first method is to E-beam evaporate from a single or from multiple crucibles metallic vapors such as FeCo or NiCo or other magnetizable materials, to cause a deposit of these materials on a wide web of inexpensive plastic such as PVC. The thickness of the deposit can be controlled as desired by, for example, varying the amount of vaporized metal. This web with, for example, 205 μm deposition thickness across a typically 1 meter width is then moved under a laser cutting station where, at the exit station, the web is cut into shaped particles that fall, like snow flakes, into a bath where the plastic becomes dissolved and the particles are magnetically extracted. After a degaussing step, the particles are collected in acetone for future use.

EXAMPLE 2

Manufacturing Method 2—Electrolytic Deposition

Figure 22:
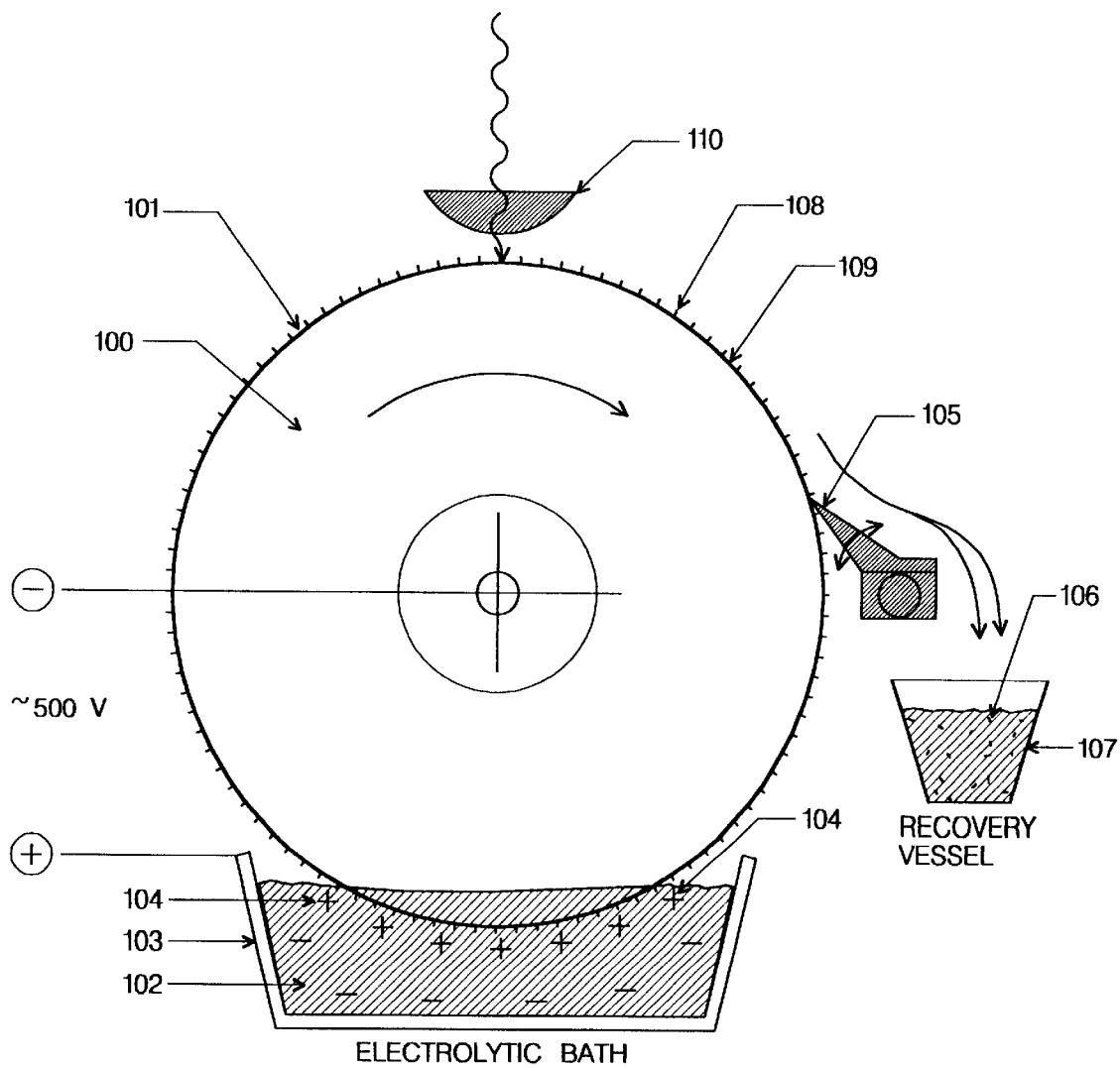
FIG. 22 depicts one preferred apparatus for manufacturing micromagnets through the process of electrolytic deposition.

While the general process of electrolytic deposition of metals is well known in the art and normally applied for decorative purposes, such as chromium deposition on car bumpers, the practical development of this process to economically fabricate small, magnetizable, substantially acicular particles of purpose-related geometries, specifically with a lengthwise dimension suited for magnetophoresis, is taught herein. This method uses a base medium which is electrically conductive and firm enough to support additional coatings as required by the method. The base medium can comprise a firm platform such as a fiberglass plate, or preferably an endless metallic belt or drum. In one embodiment, the base medium comprises at least one electrically conductive metal; preferably copper, magnesium, aluminum, gold, silver, platinum, or palladium; and may also comprise an electrically conductive, dissolvable release layer, such as a non-insulating organic layer or an electrically conductive polymer, disposed thereon. A surface layer of photoresist is then applied to the base medium to form a composite. Referring to FIG. 22, there is depicted an endless drum 100 as the base medium onto which a coating of photoresist (DuPont, Kodak, or 3M) is applied to form a surface layer 101, preferably on top of a release layer of thin electrically conductive polymer such as copper-enriched polyvinylchloride, thereby forming the base medium/surface layer composite. This photoresist, being UV light sensitive, is exposed to UV-light from a UV-light generating apparatus 110 using a perforated mask or template to not mask the areas where particles are to be fabricated by electrolytic deposition. The perforations in the template are configured so as to coincide with the geometric shape of the particles desired. If substantially homogenous microparticles are desired, the perforations should be substantially homogenous. With the exposed shaped areas being chemically etched out in a well-known procedure (for example, with solvent available from Kodak), needle-shaped pockets extending down through the surface layer to the base medium are created, with unexposed photoresist surface layers remaining and forming walls 108 which define the pockets 109. The base medium/photoresist surface layer composite is placed into an electrolytic bath 102 where the bath container 103 is electrically positive (anode), and the base medium composite is negative (cathode). As in any electrolytic bath, when a voltage is applied (for example, 500 volts) metallic ions (+) move to the cathode 104, filling pockets 109, and the non-metallic groups such as chlorides or sulfides will move to the anode, where they build up a deposit. When the endless belt moves around a tight radius roller or the photoresist surface layer 101 meets the sharp edge of a blade 105, the particles 106 will, due to their stiffness, pop out of their pockets and fall into a receptacle 107. From there the micromagnets are removed for future use. Alternatively, the composite can be subjected to treatment with solvents which soften the release layer (if present) and/or the photoresist surface layer, allowing for easier disassociation of the surface layer from the base medium by scraping and/or further solvent treatment, and whereby said surface layer is eventually dissolved, freeing said microparticles, which are then collected for later use.

EXAMPLE 3

Manufacturing Method 3—Hollow Micromagnets

To fabricate hollow particles, one prefers to use chemically-dissolvable fiber such as a plastic or metallic fiber, for example PET (polyethyltheraphilate) or copper, the outside of which is coated by vapor deposition with evaporated metal layers, for example by E-beam evaporation of desired metal from at least one crucible. Once cut to the desired length, for example by a laser, and etched, for example by chemical bath comprising an acid or an organic solvent, such as methyl ethyl ketone, the inside of each microtube can be filled with the reactive substances that suit the application. As with the solid particles, very sharp tips can be formed on both ends. Fabrication of grooved micromagnets can employ electroplating on an acid-dissolvable mask to create for example a 1 μm-deep unilateral groove behind the micromagnet point (may be solid alloy) cut on a slant for a submicron tip, for example, a 0.5 μm tip.

EXAMPLE 4
Manufacturing Method 4—Hollow Micromagnets

Another method of manufacturing hollow particles using electrically conductive plastic threads having very small diameter is by electrolytic deposition to form a metallic "skin" on the thread. The plastic thread surface is electrostatically charged and brought into contact with an electrolytic bath where a metallic "skin," preferably of FeCo or NiCo, is formed around the thread. The coated thread is then cut into tiny segments of the desired length, the segments are immersed in a bath to chemically etch out the plastic centers of the segments, the bath preferably comprising an organic solvent such as methyl ethyl ketone, thereby leaving behind the hollow metallic particles which are then collected.

EXAMPLE 5
Manufacturing Method 5—Dissolvable Particles

To produce dissolvable particles, a preferred approach is to use small particles of desired magnetizable compounds, preferably ferrite, and fill them into warm "microtubes" or "microcavities" in a mold together with, for example, a water-dissolvable binder, such as, for example, warmed glucose solution. The glucose/particulate mixture is hot-pressed, like candy, into the mold's microtubes. As the mold and glucose/particulate mixture cools, it hardens. Once hardened, the composite particles are ejected from the microcavities in the mold (preferably by air pressure or mechanical removal) and stored. After being coated with a chosen reactive substance, the particles can be injected magnetophoretically into the target site where they deliver the reactive substance and then dissolve. The magnetizable particle remnants are smaller than a red blood cell ($\cong$)30 $\mu$m and will be ejected by normal means from the human body. In plants, the ferrites will be incorporated into the plant structure, as if the ferrites had been absorbed from the ground.

EXAMPLE 6
Manufacturing Method 6—Extrusion

Extremely thin wire can be extruded by means well known in the art, and can be cut and cold-formed into the desired shape as is routine to those skilled in the art.

EXAMPLE 7
Use of Micromagnets for Penetrating Cells and Tissues

Cotton meristems from embryos dissected from imbibed seeds showed that nickel-cobalt micromagnets of lengths 50 and 100 micrometers embed quickly (within 15 seconds) in the meristem region following exposure to a magnetic field gradient from even a relatively weak quarter-inch diameter permanent magnet. Longer exposure, or pulsed exposure, results in deeper penetration. For example, after one hour of exposure, all nickel-cobalt micromagnets of 50 micrometer length have penetrated completely. Similar treatment with the permanent magnet and germinated tobacco pollen tubes resulted in quick penetration of the tube cell wall without compromising its integrity.

EXAMPLE 8
Cells and Tissues Can Be made Magnetically Reactive by Treatment with Micromagnets For lily pollen, bud-stage samples were collected on filter paper, magnetophoretically treated, resuspended in water and transferred to microscope slides for viewing and magnetic manipulations. For example, tiger lily pollen was treated with a magnetophoresis device with 1% (w/v) nickel-cobalt micromagnets of 10 micrometer length, 2 micrometer width under 4 amps (about 12,000 Gauss) for 2 minutes. Video filming on a Zeiss inverted microscope at 100 x total magnification documented individual pollen grains moving in response to a quarter-inch permanent magnet, applied externally. Some cells had one or more micromagnets visibly embedded. Such magnetically tagged cells can be magnetically tethered in one location by the external magnet, permitting static sorting while untagged cells which can be removed by gravity or gentle suction. Similar experiments were performed with micromagnets of lengths of 25 and 50 micrometers, with similar results. All magnetophoretically-treated pollen samples, but no untreated controls, had examples of pollen grains that responded to an externally applied magnetic field.

For maize pollen collected from anthers directly onto plastic Petri plates, magnetically reactive pollen was obtained by treatment with a magnetophoresis device with 1% (w/v) nickel-cobalt micromagnets of 10 micrometer length, 2 micrometer width under 12 amps (about 40,000 Gauss) for 5 seconds. Pollen was transferred to microscope slides and examined with a Zeiss inverted microscope. A half-inch cylindrical permanent magnet was used to manipulate the magnetically reactive cells while video filming at 20x total magnification. Results obtained were similar to that reported for the lily pollen in that cells could be magnetically manipulated at the discretion of the user of the external magnet.

In general, the longer the micromagnet used for embedding, the more reactive the penetrated pollen grain to the hand-held external cylindrical quarter-inch magnet. Samples with nickel-cobalt micromagnets of 50 micrometer length are much more reactive than 25 or 10 microns; the grains with nickel-cobalt micromagnets of 25 micrometer length show faster relative motion than samples with 10 micron micromagnets.

For cotton tissues, embryos from water-soaked seeds were excised, dissected longitudinally, and treated with a magnetophoresis device with 1% (w/v) nickel-cobalt micromagnets of 50 micrometer length, 2 micrometer width under 4 amps (about 8,000 Gauss) for 2 minutes in glycerol. The treated tissue is clearly embedded with a multiplicity of micromagnets. This tissue is placed adjacent to a non-treated, non-embedded dissected embryo for video taping at 10x total magnification. Under manipulation of a half-inch cylindrical permanent magnet, the magnetophoretically-treated sample is displaced and separated from the non-treated control.

EXAMPLE 9
Use of Micromagnets for Coating by Polynucleotide and Delivery and Expression of Foreign DNA in a Cell Transient expression studies were done using Black Mexican Sweet maize suspension cells, 3-day old, plated onto filter paper supports as shallow-mounded cells of 250 microliter packed cell volume (<3 mm high). Nickel-cobalt micromagnets of 50 micrometer length, about 2 micron width, were used after coating in spermidine/calcium chloride as is known in the art, modified such that no final ethanol rinse was made and 2 micrograms DNA plasmid (pAGM100) were used per 50 microliter coating mix. Aliquots of 10 microliter, 0.01% (w/v) micromagnets, were applied to cells, treated with a magnetophoresis device under 4 to 6 amps (about 15,000 to 20,000 Gauss) for 30 seconds. Cells were transferred to a microscope slide for viewing with a Nikon compound microscope 1 day after staining in GUS solution as is known in the art. GUS-positive blue foci were obtained in samples treated by magnetophoresis while none were observed in the untreated controls. Different studies confirmed these observations using different length micromagnets and varying treatment conditions.

EXAMPLE 10
Use of Micromagnets for Magnetic Treatment of Human Cancer Cells

Breast cancer cell line MDA MB435 was grown as a monolayer in Richters growth medium under carbon dioxide as is known in the art. Excess growth medium was removed and the plate bottom marked to indicate where micromagnets would be convergently applied. Cancer cells were penetrated by micromagnets after being treated magnetophoretically with 0.1% (w/v) nickel-cobalt micromagnets of 10 and 100 micrometer length, 2 micrometer width (subcellular and supercellular dimensions, respectively) under 4 amps (about 12,000 Gauss) for 30 seconds. The shorter micromagnets were observed in elongated cells of G1 or S phase cells as seen by focussing at 100 × on a Zeiss inverted microscope. The longer micromagnets were clearly seen to have speared predominantly the round G2 or M phase cells, with some not adherent to the plate.

EXAMPLE 11
Use of Micromagnets for Mechanical Targeting into Tissues

Tobacco leaves were harvested from aseptically grown plants on Murashige and Skoog medium as is known in the art. Epidermal (trichome) and mesophyll cells were penetrated by micromagnets after being treated manually for 5 to 7 minutes with 0.1% (w/v) nickel-cobalt micromagnets of 100 micrometer length, 2 micrometer width, coated using stationary coating with the standard spermidine/calcium chloride precipitation mix with DNA of pAGM148 (10 microgram). Micromagnets were mounted vertically and in parallel on a ceramic permanent bar magnet on top, opposed in parallel by two ceramic permanent magnets on the bottom to form a sandwich around the leaf (crushing was prevented by cork spacers). Micromagnets were maintained rigid and oriented in the vertical and did not buckle during manual compression of the sandwich, as observed at 8 × on a Zeiss dissecting microscope. The bar magnets were pulled apart and leaf tissues were placed in GUS staining solution with 20% methanol. Blue GUS positive trichomes and mesophyll cells were observed within hours in mechanically treated tissues but not in untreated control tissues. In another example, a cold-formed stainless steel micromagnet of about 2000 microns length was manually placed above the apex of a dissected carnation shoot tip, laying on top of the tissue. The tissue-micromagnet assembly was placed for less than 30 seconds in the path of a converging field from a quarter-inch cylindrical permanent magnet. Observation on a dissecting microscope showed that the micromagnet had oriented perpendicular to the apex surface, along field lines, and had penetrated the apical dome of the meristem.

It should be understood that the examples and embodiments described herein are for illustrative purposes only and that various modifications or changes in light thereof will be suggested to persons skilled in the art and are to be included within the spirit and purview of this application and the scope of the appended claims.

References

Allen, L. M., Kent, T., Wolfe, C. et al. (1997) "Scientific and Clinical Application of Magnetic Carriers." Haefeli et al., eds. Plenum Press, New York.

Matthews (1997). Plant Virology, $3^{rd}$ ed. Academic Press, San Diego.

Maulik, S., Patel, S. D. (1997) *Molecular Biotechnology*. "Therapeutic Applications and Strategies." Wiley-Liss, New York.

Tibbe AGJ, de Grooth BG, Greve J., Liberti PA, Dolan GJ, Terstappen I., WMM (1999). Optical tracking and detection of immunomagnetically selected and aligned cells. *Nature Biotechnology* 17:1210-1213.

U.S. Pat. No. 4,345,588, issued Aug. 24, 1982 to Wideder, K. J., Senyel, A. E., entitled "Method of Delivering a Therapeutic Agent to a Target Capillary Bed."

U.S. Pat. No. 4,554,088, issued Nov. 19, 1985 to Whitehead, R. A., Chagnon, M. S., Groman, E. V., Josephson, L., entitled Magnetic Particles for Use in Separations.

U.S. Pat. No. 5,698,271; Issued Dec. 16, 1997 to Liberti, P. A, Rao G. C., Chiarappa, J. N., entitled "Methods for the Manufacture of Magnetically Responsive Particles."

What is claimed is:

1. A method of making magnetizable microparticles, comprising the steps of:
    providing an electrically conductive base medium;
    depositing a layer of photoresist on said base medium to yield a composite comprising said base medium and a surface layer of photoresist;
    exposing portions of said surface layer to an ultraviolet light source;
    etching said surface layer with photoresist solvent, thereby producing microcavities of a predominantly lengthwise dimension in said surface layer;
    contacting said surface layer with an electrolytic bath, said bath being in a container and comprising metallic salts or alkaline combined ions, such that upon the application of voltage to said bath, said composite acts as a cathode and said container acts as an anode;
    applying voltage to said bath, whereby metal ions in said bath move toward said surface layer and are therein deposited in said microcavities wherein they form magnetizable microparticles;
    freeing said magnetizable microparticles from said surface layer; and
    collecting said microparticles.

2. A method according to claim 1, wherein said electrically conductive base medium comprises at least one electrically conductive metal.

3. A method according to claim 2, wherein said electrically conductive base medium comprises at least one metal selected from the group consisting of copper, magnesium, aluminum, gold, silver, platinum, and palladium.

4. The method according to claim 3, wherein said metal is selected from the group consisting of copper, magnesium, and aluminum.

5. The method according to claim 1, wherein said ultraviolet light source is selected from the group consisting of an electron beam and a laser beam.

6. A method according to claim 1, wherein said electrically conductive base medium comprises an electrically conductive, chemically dissolvable release layer disposed beneath said surface layer.

7. A method according to claim 1, wherein said freeing step is accomplished by dissolving said photoresist.

8. A method according to claim 1, wherein said electrically conductive base medium is an endless medium selected from the group consisting of an electrically conductive belt and an electrically conductive drum.

9. A method according to claim 1, further comprising the step of applying a mask to said photoresist surface layer, said mask having perforations therein through which ultraviolet light can pass to expose those portions of said photoresist surface layer not covered by the unperforated portions of said mask.

10. A method according to claim 9, wherein said perforations are of substantially uniform dimension.

11. A method according to claim 10, wherein said microcavities are of substantially uniform dimension, thereby yielding a uniform assemblage of microparticles.

12. A method according to claim 1, further comprising the step of disassociating said surface layer from said base medium.

13. A method of making hollow or grooved magnetizable microparticles, comprising the steps of:
providing a microfiber comprising a chemically dissolvable compound;
applying a magnetizable metal layer to at least a portion of the surface of said fiber;
cutting said fiber into microsegments of desired length;
dissolving said fiber, thereby leaving behind magnetizable microparticles; and
collecting said magnetizable microparticles.

14. The method according to claim 13, wherein said fiber comprises at least one compound selected from the group consisting of plastics and copper.

15. A method according to claim 13, wherein said applying step is accomplished by vapor deposition of metal.

16. A method according to claim 13, wherein said applying step is accomplished by electroplating.

17. A method according to claim 16, further comprising the step of rendering said fiber electrically conductive.

18. A method according to claim 17, further comprising the step of placing said electrically conductive fiber in an electrolytic bath.

19. A method of making composite water-dissolvable magnetizable particles, comprising the steps of:
providing a mold comprising a plurality of microcavities of a predominantly lengthwise dimension;
providing a moldable composition comprising microscopic magnetizable particles and a water-dissolvable binder;
forcing said composite into said microdepressions of said mold;
allowing said composite to harden in said mold; and
removing said hardened composite from said mold, whereby water-dissolvable magnetizable particles are obtained.

20. A method according to claim 19, wherein said microscopic particles comprise ferrite.

21. A method according to claim 19, wherein said water-dissolvable binder comprises glucose.

22. A method of making magnetizable microparticles, comprising the steps of;
providing a plastic webbed substrate;
applying a magnetizable metal layer to at least a portion of said substrate;
cutting said substrate into shaped microparticles;
dissolving said plastic, thereby leaving behind said magnetizable microparticles; and
collecting said magnetizable microparticles.

23. A method according to claim 22, wherein said applying step is accomplished by vapor deposition of metal.

24. A method according to claim 22, wherein said cutting step comprises contacting said substrate with a laser.

25. A magnetizable microparticle of from 2 microns to 1,000 microns in length, and having a length to width ratio of from 4:1 to 500:1; said microparticle having a sharp tip at one end and a broader portion at the other end.

26. A magnetizable microparticle according to claim 25, wherein said broader portion is a nail-head-like tail.

27. A magnetizable microparticle of from 2 microns to 1,000 microns in length, and having a length to width ratio of from 4:1 to 500:1; said microparticle comprising at least one internal cavity and at least one external opening accessing said at least one cavity.

28. A magnetizable microparticle according to claim 27, wherein said microparticle comprises a plurality of said external openings.

29. A magnetizable microparticle according to claim 28, comprising two external openings.

30. A magnetizable microparticle of from 2 microns to 1,000 microns in length, and having a length to width ratio of from 4:1 to 500:1; said microparticle comprising at least one longitudinal groove extending more than half of the length of the microparticle.

31. A magnetizable microparticle of from 2 microns to 1,000 microns in length, and having a length to width ratio of from 4:1 to 500:1; said microparticle comprising a radioactive substance.

32. A magnetizable microparticle according to claim 31, wherein said microparticle comprises cobalt.

33. A magnetizable microparticle according to claim 32, further comprising nickel.

34. A magnetizable microparticle according to claim 32, further comprising iron.

35. A magnetizable microparticle of from 2 microns to 1,000 microns in length, and having a length to width ratio of from 4:1 to 500:1; said microparticle comprising an electric insulation material.

36. A magnetizable microparticle according to claim 35, wherein said electrical insulation material is selected from the group consisting of $SiO_2$ and $Si_3N_4$.

37. A magnetizable microparticle of from 2 microns to 1,000 microns in length, and having a length to width ratio of from 4:1 to 500:1; said microparticle comprising a solidified water-dissolvable binder and a plurality of magnetizable particles embedded therein.

38. A magnetizable microparticle of from 2 microns to 1,000 microns in length, and having a length to width ratio of from 4:1 to 500:1; said microparticle comprising at least one payload area disposed between the ends of said microparticle, said payload area having a reduced diameter as compared to the diameter of at least two other portions of the microparticle between the ends.

39. A magnetizable microparticle according to claim 38, comprising a plurality of payload areas.

* * * * *

UNITED STATES PATENT AND TRADEMARK OFFICE
CERTIFICATE OF CORRECTION

PATENT NO. : 6,706,394 B2
DATED : March 16, 2004
INVENTOR(S) : Adelheid R. Kuehnle and Manfred R. Kuehnle It is certified that error appears in the above-identified patent and that said Letters Patent is hereby corrected as shown below:

Column 6,
Line 63, "ends thereof Mounted in holes" should read -- ends thereof. Mounted in holes --

Column 7,
Line 61, "and Area -1 is the volume" should read -- and Area -$l$ is the volume --.

Column 16,
Line 39, "stiffiess" should read -- stiffness --.

Signed and Sealed this

Twenty-first Day of September, 2004

JON W. DUDAS
*Director of the United States Patent and Trademark Office*